United States Patent [19]

Kabasakalian et al.

[11] 4,027,016

[45] May 31, 1977

[54] EVERNINOMICIN ANTIBACTERIAL DERIVATIVES, ELECTROCHEMICAL METHOD FOR THEIR MANUFACTURE, METHOD FOR THEIR USE AS ANTIBACTERIAL AGENTS, AND PHARMACEUTICAL COMPOSITIONS USEFUL THEREFOR

[75] Inventors: Peter Kabasakalian, Bloomfield; Sami Y. Kalliney, Parsippany; Ashit K. Ganguly, Upper Montclair; Anita Westcott, Montclair, all of N.J.

[73] Assignee: Schering Corporation, Kenilworth, N.J.

[22] Filed: Jan. 19, 1976

[21] Appl. No.: 650,081

[52] U.S. Cl. .............................. 424/180; 204/73 R; 536/17; 536/18
[51] Int. Cl.² ........................................ A61K 31/715
[58] Field of Search ................ 536/17, 18; 424/180

[56] References Cited

UNITED STATES PATENTS

| | | | |
|---|---|---|---|
| 3,915,956 | 10/1975 | Ganguly | 536/17 |
| 3,920,629 | 11/1975 | Ganguly | 536/17 |
| 3,998,708 | 12/1976 | Kabasakalian et al. | 204/59 R |

*Primary Examiner*—Johnnie R. Brown
*Attorney, Agent, or Firm*—Mary S. King; Stephen B. Coan

[57] ABSTRACT

Everninomicin derivatives devoid of a nitro group and having antibacterial activity are prepared by electrochemically reducing the corresponding everninomicin having a nitro function or salts thereof in an aprotic anhydrous solvent in the absence of carbon dioxide. A preferred starting compound is everninomicin D whereby is produced a product mixture of antibacterial agents identified as desevernitrose everninomicin D, everninomicin D-3, and everninomicin D-7, respectively.

11 Claims, 2 Drawing Figures

NUCLEAR MAGNETIC RESONANCE SPECTRUM OF EVERNINOMICIN D-3

Fig. 1

NUCLEAR MAGNETIC RESONANCE SPECTRUM OF EVERNINOMICIN D-7

Fig. 2

EVERNINOMICIN ANTIBACTERIAL DERIVATIVES, ELECTROCHEMICAL METHOD FOR THEIR MANUFACTURE, METHOD FOR THEIR USE AS ANTIBACTERIAL AGENTS, AND PHARMACEUTICAL COMPOSITIONS USEFUL THEREFOR

FIELD OF INVENTION

This invention relates to novel compositions of matter, to methods for their manufacture, to methods for their use as antibacterial agents, and to pharmaceutical compositions useful therefor.

More specifically, this invention relates to novel antibacterial derivatives of everninomicins B, C and D, which are devoid of nitrogen, and their method of manufacture by the electrochemical reduction of the corresponding everninomicin having a nitro function or of salts thereof, in an anhydrous aprotic solvent in the absence of carbon dioxide.

In particular, this invention relates to novel everninomicin derivatives identified as everninomicins B-3, C-3 and D-3 and everninomicins B-7, C-7 and D-7 which are prepared together with desevernitrose everninomicin B, desevernitrose everninomicin C and desevernitrose everninomicin D; from the corresponding everninomicin or salt thereof upon the electrochemical reduction thereof in an anhydrous aprotic solvent in the absence of carbon dioxide.

This invention also relates to the method of using everninomicins B-3, C-3, D-3, and B-7, C-7 and D-7 as antibacterial agents and to pharmaceutical compositions useful therefor.

PRIOR ART

A mixture of everninomicin antibiotics, including everninomicin B, everninomicin C and everninomicin D, is produced when *Micromonospora carbonacea var. carbonacea* and a variant thereof, *Micromonospora carbonacea var. aurantiacia*, are subjected to submerged aerobic fermentation under conditions described in U.S. Pat. No. 3,499,078.

Upon reduction with aluminum amalgam according to procedures described in U.S. Pat. No. 3,915,956, the nitro group in the everninomicins is reduced to a nitroso function or to a hydroxylamine to produce the corresponding nitrosoeverninomicins B, C or D and the corresponding hydroxylaminoeverninomicins B, C or D, all of which exhibit antibacterial activity.

When a nitrosoeverninomicin is treated with a phosphorous reagent such as triethylphosphite or triphenylphosphene according to procedures such as described in U.S. Pat. No. 3,920,629, there is produced the corresponding desevernitrose derivative, i.e. desevernitrose everninomicin B, desevernitrose everninomicin C and desevernitrose everninomicin D, having anti-bacterial activity.

By the invention of this application, we have found that when an everninomicin or a salt thereof is electrochemically reduced in an anhydrous aprotic solvent in the absence of carbon dioxide, there is produced a mixture of anti-bacterial agents all of which are devoid of nitrogen, said mixture comprising two novel antibacterial agents identified as the corresponding everninomicin 3 and everninomicin 7 in admixture with the corresponding desevernitrose everninomicins which are known antibacterial agents. By our invention, we have also discovered that the electrochemical reduction may be carried out in the presence of oxygen, but is preferably carried out in an inert medium in the absence of carbon dioxide.

In a preferred mode of our invention, everninomicin D or a salt thereof is electrochemically reduced in anhydrous dimethylformamide in the presence of argon to produce a product mixture comprising desevernitrose everninomicin D (a known antibacterial agent) in admixture with everninomicin D-3 and everninomicin D-7.

GENERAL DESCRIPTION OF THE COMPOSITION-OF-MATTER ASPECT OF THE INVENTION

Included within the composition-of-matter aspect of this invention are everninomicin antibacterial derivatives devoid of nitrogen selected from the group consisting of everninomicin B-3, everninomicin C-3, everninomicin D-3, everninomicin B-7, everninomicin C-7, everninomicin D-7, and the pharmaceutically acceptable phenolic mono-cationic salts and N-methylglucamine acid addition salts of the foregoing, said everninomicin derivatives being represented by the following formula I:

wherein
X is a member selected from the group consisting of

Y is a member selected from the group consisting of hydrogen and hydroxyl;

Z is a member selected from the group consisting of and hydrogen provided Y is hydrogen; and said pharmaceutically acceptable salts are salts of the phenol substituent in said everninomicin derivative.

As established by Nuclear Magnetic Resonance (nmr) spectra, the everninomicin -3 products are reproducible mixtures of compounds of formula I wherein X is a substituent selected from the group consisting of 3-exodehydro-3-desnitroevernitrose, 2-dehydro-3-desnitroevernitrose, and 3-dehydro-3-desnitroevernitrose; whereas the everninomicin -7 derivatives are compounds of formula I wherein X is 3-hydroxy-3-desnitroevernitrose. Thus, everninomicin B-3 is a compound of formula I wherein Y is hydroxyl, Z is and X is while everninomicin B-7 is a compound of formula I wherein Y and Z are the same as in B-3, but X is Similarly, everninomicin C-3 is a compound of formula I wherein Y and Z are each hydrogen and X is as defined for everninomicin B-3, while in everninomicin C-7, Y and Z are each hydrogen and X is as defined for everninomicin B-7; everninomicin D-3 is a compound of formula I wherein Y is hydrogen, Z is and X is as defined for everninomicins B-3 and C-3, and everninomicin D-7 is a compound of formula I wherein Y and Z are the same as in everninomicin D-3, but wherein X is the same as in B-7 and C-7.

Preferred compounds of this invention are those derived from everninomicin D, i.e. everninomicin D-3 and everninomicin D-7, which are particularly effective in inhibiting the growth of gram-positive bacteria. Advantageously, certain gram-negative bacteria are also susceptible to (i.e. their growth is inhibited by) everninomicins D-3 and D-7.

The physical embodiments of the everninomicin derivatives of formula I are colorless crystalline solids which are soluble in most organic solvents, particularly in hydrocarbons such as benzene, xylene and toluene and in cyclic ethers such as tetrahydrofuran and dioxane, being less soluble in dialkyl ethers such as ethyl ether. As is evident from formula I, the everninomicin -3 and -7 derivatives of this invention are oligosaccharides, each containing a dichloroisoeverninoyl ester grouping, several anomerically linked monosaccharide groups and two ortho ester functions. It is known that ortho esters hydrolyze readily in acidic medium. In view of the presence of these functions in our compounds, in order to minimize side reactions it is preferable to store the everninomicin -3 and -7 derivatives under anhydrous conditions in an inert atmosphere (e.g. under nitrogen, argon, etc.) at low temperatures (i.e. at about 5°–10° C).

The everninomicin —3 and everninomicin —7 derivatives of this invention contain an acidic phenolic hydroxyl function which is readily convertible to pharmaceutically acceptable salts thereof utilizing procedures known in the art. Among the pharmaceutically acceptable phenolic salts contemplated for this invention are cationic salts of alkali and alkaline earth metals (e.g. sodium, potassium, calcium, magnesium) and acid addition salts with an amine such as a trialkylamine, procaine, dibenzylamine, N-benzylbetaphenethylamine, N,N'-dibenzylethylenediamine, N,N'-bis-dehydroabietylethylenediamine, N-(lower) alkyl-piperidines (e.g. N-ethylpiperidine) and, preferably, the N-methylglucamine salts of the everninomicin -3 and everninomicin -7 derivatives. Thus, the pharmaceutically acceptable salts of this invention include those which replace the phenolic hydrogen with a cation (e.g. everninomicin D-7 sodium salt) and those wherein the phenolic hydrogen and everninomicin radical form an acid addition salt with an amine (e.g. everninomicin D-7 N-methylglucamine salt).

Included among the pharmaceutically acceptable salts of this invention are:
everninomicin B-3 sodium salt and N-methylglucamine salt,
everninomicin B-7 sodium salt and N-methylglucamine salt,
everninomicin C-3 sodium salt and N-methylglucamine salt,
everninomicin C-7 sodium salt and N-methylglucamine salt,
everninomicin D-3 sodium salt and N-methylglucamine salt,
everninomicin D-7 sodium salt and N-methylglucamine salt.

The cationic salts (e.g. the sodium salt) are prepared according to known procedures such as by combining equimolar quantities of the corresponding base (e.g. sodium hydroxide) to the everninomicin —3 or everninomicin —7 derivative (e.g. everninomicin D-7) in water and lyophilizing the resultant solution of the everninomicin D-7 salt. The amine acid addition salts are prepared by combining equimolar quantities of the amine (e.g. N-methylglucamine) to the everninomicin derivative (e.g. everninomicin D-7) in a lower alkanol and isolating the solvent in vacuo or by precipitation with ether.

The pharmaceutically acceptable salts of our invention are white amorphous solids which are water soluble and form stable aqueous solutions. They are, therefore, a particularly preferred species of our invention since they are a convenient vehicle for administering the everninomicins —3 and everninomicins —7 of our invention.

The everninomicins B-3, B-7, C-3, C-7, D-3 and D-7 of this invention including the pharmaceutically acceptable salts thereof, particularly the preferred everninomicin D-7 and the sodium and N-methylglucamine salts thereof, exhibit a narrow spectrum antibacterial activity in vitro against gram-positive bacteria (e.g. *Staphylococcus aureus*, Staph. 11631, Staph. W., *Streptococcus pyogenes* C, *Strep. pyogenes* C-203 and *Bacillus subtilis*). Our compounds are thus advantageously employed as laboratory reagents when attempting to determine the presence of enteric gram-negative organisms. They may be used to inhibit overgrowth of gram-positive organisms in culture media, either alone or in combination with other antibacterial agents to reduce or eliminate the heavy overgrowth of gram-positive organisms permitting the determination of gram-negative organisms such as *Klebsiella pneumoniae* or *Escherichia coli* in cultures obtained in diagnostic procedures. As such reagents they may be used to "sterilize" equipment such as in operating rooms and in hospital wards.

The comparative in vitro activities of everninomicin D-3, everninomicin D-7, and of hydroxylaminoeverninomicin D sodium salt are set forth in Table 1 hereinbelow:

Table 1

| Microbiological Activity (in vitro) MIC's mcg/ml | Everninomicin D-3 | Everninomicin D-7 | Hydroxylaminoeverninomicin D Sodium salt |
|---|---|---|---|
| Staphylococcus aureus Strain | | | |
| 209B | 0.06 | 0.3 | 0.06 |
| Gray | 0.06 | 0.3 | 0.06 |
| 59N | 0.03 | 0.075 | 0.03 |
| Ziegler | 0.03 | 0.75 | 0.06 |
| Wood | 0.06 | 0.75 | 0.06 |
| Microbiological Activity (in vivo) PD$_{50}$'s (mg/kg) s.c. | | | |
| Staphylococcus | 0.5 | 1–5 | 0.5–5 |
| Peak Serum Levels in Dogs, 10 mg/kg i.m. | 12–16 | 15–60 | 20–30 |

In above Table 1, there is also listed in vivo data for the peak serum levels in dogs, as well as PD$_{50}$ doses in mice for hydroxylaminoeverninomicin D sodium salt, everninomicin D-3, and everninomicin D-7 against Staphylococcus.

The protection tests to determine the dose required to protect fifty percent of the animals tested (PD$_{50}$) use groups of seven mice (male albino CF-1 mice, each weighing 18-20 g.) each at five dose levels with 10 mice serving as controls. Mice were each treated with a single subcutaneous or oral dose one hour after intraperitoneal infection with approximately $10^7$ organisms. Control mice were generally dead 18–24 hours after infection. Survivors in treated groups were determined 48 hours after infection. Probit procedures were used to determine PD$_{50}$ values in milligrams per kilogram.

In determining peak serum levels, the animal tested (e.g. dog) is given a single dose of 10 mg/kg of the everninomicin D derivative, blood samples are taken periodically, and the serum thereof is assayed for antibacterial activity by an agardiffusion-assay as described by Weinstein et al., *Antimicrobial Agents and Chemotherapy*, p. 24 (1964).

It is apparent from the foregoing that, when administered by injection, everninomicin D-3 and D-7 exhibit antibacterial activity comparable to that of the precursor hydroxylaminoeverninomicin D, being particularly effective in inhibiting the growth of gram-positive bacteria and, advantageously, are also rapidly absorbed, producing high serum levels in the dog. Therefore, everninomicins D-3 and D-7 and salts thereof are among the preferred compounds of this invention.

GENERAL DESCRIPTION OF THE PROCESS ASPECT OF THE INVENTION

The process sought to be patented comprises electrochemically reducing an everninomicin selected from the group consisting of everninomicin B, everninomicin C, everninomicin D, and phenolic mono-cationic salts and N-methylglucamine acid addition salts of the foregoing, at a cathode potential of about at least as negative as the lowest potential on the rising portion of the polarographic current-potential (i.e. i-E) curve of said everninomicin in an anhydrous aprotic solvent in the absence of carbon dioxide, and with an electrolyte comprising a difficultly reducible cation selected from the group consisting of alkali metal, and substituted ammonium ions (e.g. a tetraalkylammonium salt such as tetrabutylammonium chloride) whereby is produced a product comprising a member selected from the group consisting of the corresponding desevernitrose everninomicin, the corresponding everninomicin 3, the corresponding everninomicin 7, and mixtures thereof.

The preferred starting compounds for our process are everninomicin antibiotics having a nitro group, particularly everninomicin B, everninomicin C, and everninomicin D which are known antibiotics produced by the aerobic fermentation of *Micromonospora carbonacea var. carbonacea* and a variant thereof, *Micromonospora carbonacea var. aurantia* according to procedures known in the art such as described in U.S. Pat. No. 3,499,078. The isolation and purification of everninomicins B and D are carried out essentially as described in the art and the isolation, purification and characterization of everninomicin C are carried out in similar fashion as disclosed in U.S. Pat. No. 3,915,956.

Of antibiotics everninomicins B, C and D, everninomicin D is the most readily available and is a preferred starting compound for our electrochemical reduction process since there is produced therefrom preferred compounds of this invention, i.e. everninomicin D-3 and everninomicin D-7, valuable antibacterial agents.

The everninomicin starting compounds of our invention are compounds of the following structural formula II wherein X' is nitro (i.e. X' is and wherein, the everninomicin B, Y is hydroxyl and Z is in everninomicin C, Y and Z are hydrogen; and in everninomicin D, Y is hydrogen and Z is

The above-listed everninomicin starting compounds of our invention all contain a phenolic hydroxyl function which is readily convertible to salts thereof, utilizing procedures known in the art. Such salts may also be used as starting compounds in our electrochemical reduction process and are considered as equivalent to their free everninomicin or nitrosoeverninomicin precursors, including salts of alkali metals (e.g. sodium, potassium) and salts with an amine (e.g. trialkylamines and N-methylglucamine).

Our electrochemical reduction process consists essentially of reducing the nitro function (i.e. X') in everninomicins B, C or D to an anion radical followed by rearrangement, whereby are formed everninomicin 3 and everninomicin 7 derivatives of this invention.

Also produced by our electrochemical process are the corresponding desevernitrose everninomicins, i.e. compounds wherein the evernitrose radical (i.e).

is removed and replaced by hydrogen. The desevernitrose everninomicins are antibacterial agents described in U.S. Pat. No. 3,920,629 and are compounds of formula I wherein X is hydrogen and Y and Z are as defined hereinabove for formulae I and II. Thus, desevernitrose everninomicin B is a compound of formula I wherein X is hydrogen, Y is hydroxyl and Z is desevernitrose everninomicin C is a compound of formula I wherein X, Y and Z are hydrogen, and desevernitrose everninomicin D is a compound of formula III wherein X and Y are hydrogen and Z is Our electrochemical process whereby an everninomicin or a phenolic salt thereof is converted to the corresponding desevernitrose everninomicin, or to the corresponding everninomicin —3 or to the corresponding everninomicin —7 or to mixtures thereof, is carried out in an anhydrous, aprotic solvent in the absence of carbon dioxide. If carbon dioxide is present in any great amount, the compounds of this invention are not formed but, rather, there is produced the corresponding hydroxylaminoeverninomicin in high yields as disclosed in our co-pending application Ser. No. 650,082 filed simultaneously with the instant application, now U.S. Pat. No. 3,998,708. Additionally, our process is preferably carried out in an anhydrous aprotic solvent since, in the presence of water, under the electrochemical conditions of our process, there would also be produced the hydroxylaminoeverninomicin derivative corresponding to the starting everninomicin.

In our electrochemical process, any anhydrous aprotic solvent may be used which does not reduce before the everninomicin or nitrosoeverninomicin to be reduced, and in which the starting compound and desired electrolyte is reasonably soluble. Useful aprotic solvents include nitriles such as acetonitriles, and N-substituted amides such as dimethylformamide, diethylacetamide and the like. We usually prefer to use acetonitrile or dimethylformamide.

Our electrochemical process is preferably carried out under an inert atmosphere other than carbon dioxide, e.g. argon or nitrogen, whereby there is usually obtained a mixture comprising the corresponding desevernitrosoeverninomicin, everninomicin 3 and everninomicin 7, with a total product yield of over 85% theory. Our electrochemical process may also be carried out in the presence of oxygen (e.g. by bubbling air or oxygen through the catholyte and anolyte during the electrolysis); however, the total yield of the everninomicin derivatives is usually thereby reduced.

Our novel electrochemical reduction process preferentially utilizes an electrolytic cell containing a mercury or mercury amalgam cathode and an electrolyte comprising a substituted ammonium salt such as tetrabutylammonium chloride. Although mercury is preferred, the cathodes can be made of any conducting material possessing a high hydrogen over-voltage.

Salts which are useful as electrolyes are those possessing a difficultly reducible cation and which are sufficiently soluble in the solvent system in the electrolytic cell to give reasonably good conductance. Salts useful as electrolytes include halides of alkali metals, such as lithium, sodium, potassium, rubidium, and the like. However, preferred electrolytes include substituted ammonium salts (preferably tetraalkyl substituted) such as tetraethylammonium bromide, tetrabutylammonium hydroxide, tetraethylammonium fluoborate, triethylmonobutylammonium chloride, tetraethylammonium perchlorate, and the like, as well as mixtures thereof such as a mixture of tetraethylammonium bromide and tetrabutylammonium bromide in dimethylformamide. Additionally, particularly preferred electrolytes are alkali metal fluoborates, particularly sodium fluoborate.

According to our process, an everninomicin or a salt thereof may be electrochemically reduced at a negative potential at least as negative as the lowest potential on the rising portion of the current-potential (i-E) curve of the everninomicin, said i-E curve being obtained under conditions similar to those used in the reduction. The i-E curve of a compound may be obtained in a variety of ways such as by utilizing a recording polarograph, or by connecting a recording potentiometer across the electrolysis cell circuit and measuring the i-E curve under the conditions of the reduction run.

The current-potential reduction curve is known to be reproducible for a given compound under a given pH and a given set of conditions and, in fact, can be used as an analytical tool for identification purposes. It is also known that the i-E reduction curve varies with the pH, solvent and electrolyte used. It is therefore preferable for carrying out our process to determine the i-E curve of each everninomicin under conditions essentially identical to those to be used during the reduction itself. However, polarograms of said everninomicins cannot be obtained in the presence of oxygen, since oxygen reduces before the everninomicins. Thus, electrochemical reductions carried out in the presence of oxygen are run at negative potentials determined from an i-E reduction curve obtained polarographically in a system excluding oxygen but utilizing the same electrolytic cell, solvent, electrolyte starting everninomicin, etc. to be used in the reduction. For example, if everninomicin D is to be reduced in anhydrous dimethylformamide in the presence of oxygen utilizing an electrolytic cell having a mercury cathode, a platinum anode, and sodium fluoborate as electrolyte, prior to reduction it is most desirable to have the current-potential curve determined polarographically on an anhydrous dimethylformamide solution of everninomicin D under an inert atmosphere, e.g. argon, utilizing sodium fluoborate as electrolyte. When a polarogrram or i-E curve for a given compound is known, one can then electrochemically reduce said compound either under an inert atmosphere or in the presence of oxygen at any potential on the rising portion of the current-voltage curve utilizing solvent, electrolyte, etc., identical to that employed when determining the polarogram (i-E curve).

A specific i-E reduction curve for a compound is, in part, a measure of the range of potential at which a compound such as everninomicin D will become reduced at the cathode, which property varies at different pH values and with different solvents. The i-E reduction curves for compounds such as the everninomicins consist of three distinct sections and are S-shaped similar to the titration curve of a strong acid and base. The first portion (i.e. pre-reduction portion) consists of an essentially flat plateau having a constant small current value, since, without reduction of the everninomicin taking place, there is no increase in the current flowing through the cell. The beginning of the rising portion of the i-E curve defines the lowest potential at which the everninomicin will become reduced at the cathode. The cathode voltage at the mid-point of the rising portion of the i-E curve is defined as the "half-wave potential." Under a given set of conditions the half-wave potential of the i-E curve is a characterizing constant of the compound.

When reducing an everninomicin derivative by our novel process, it is advantageous not to use a potential more negative than the maximum potential on the rising portion of the i-E curve. If a more negative potential is used, competing reactions may take place such as reduction of the solvent or electrolyte. When reducing an everninomicin or salt thereof, we prefer to use a potential in the range of from the half-wave potential to amount 0.3 to 0.4 volts more negative than the half-wave potential of the rising portion of the i-E curve of the everninomicin derivative being reduced. The potential usually used in the process of this invention is in the range of from about $-1.75$ to about $-1.85$ volts vs. a saturated calomel electrode (SCE).

It is evident from the foregoing that there are countless variations of electrolytic cells which may be used when electrolytically reducing an everninomicin. Cells which are particularly useful for reducing the everninomicins are those having a three-electrode system with a saturated calomel reference electrode as well as a cathode and anode, wherein the anode and anolyte are separated from the cathode and catholyte by a porous Alundum cup, and which have a mercury cathode, a graphite anode and an electrolyte comprising a tetraalkylammonium salt. Thus, for example, the reduction of an everninomicin such as everninomicin D or salt thereof, e.g. the tetraethylammonium salt, may be effected by dissolving the everninomicin or salt thereof (e.g. the tetraethylammonium salt of everninomicin D) in an anhydrous aprotic solvent containing an electrolyte (e.g. 0.01 molar tetraethylammonium fluoborate) and placing the solution in the cathode compartment of a three-electrode system cell such as described hereinabove; also placing a solution of an electrolyte (which may be the same or different as that in the catholyte) in the same anhydrous solvent (e.g. 0.01 molar tetraethylammonium iodide in anhydrous dimethylformamide) in the anode compartment; bubbling a gas other than carbon dioxide, i.e. either an inert gas (e.g. argon) or air or oxygen through both the anolyte and catholyte solutions prior to carrying out the electrolysis, and, while continuing to bubble a gas (e.g. argon) through the electrolytes, to carry out the electrolysis at −1.8 volts vs. SCE until the reduction is complete as evidenced by the drop in current to a constant value or by polarography on deoxygenated aliquots of the solutions being reduced. The reduced product mixture (e.g. desevernitroseverninomicin D in admixture with everninomicin D-3 and everninomicin D-7) is then isolated, separated, and purified utilizing known techniques, usually chromatographic techniques, to obtain each of the antibacterial agents thereby produced.

We have discussed in detail the preferred species of our invention relating to everninomicin D-7 derivatives. In similar manner, our invention is carried out to produce antibacterial substances which are derivatives of everninomicin B and everninomicin C. Thus, everninomicins B and C, and mono-cationic and amine acid addition salts thereof, e.g. the sodium and N-methylglucamine salts, respectively, upon electrochemical recuction in an anhydrous aprotic solvent in the absence of carbon dioxide, are converted to the corresponding everninomicins B-3, B-7, C-3 and C-7, respectively, having antibacterial activity against gram-positive bacteria in admixture with the corresponding desevernitrose derivatives. Advantageously, everninomicins B-3 and B-7, C-3 and C-7, and D-3 and D-7 and pharmaceutically acceptable salts thereof exhibit antibacterial activity against bacteria which are resistant to other antibacterial agents such as penicillin, penicillinase-resistant penicillins, tetracycline, macrolide antibacterials such as erythomycin and lincomycin.

Procedures are set forth hereinbelow to illustrate the best mode contemplated by applicants for carrying out their invention and are not to be construed as limiting the scope thereof.

Preparation 1

Tetraethylammonium Salts of the Everninomicins

A. The Tetraethylammonium Salt of Everninomicin D

To a suspension of everninomicin D in water under an atmosphere of nitrogen, slowly add an aqueous solution of a equivalent quantity of tetraethylammonium hydroxide. Lyophilize to obtain a residue comprising the tetraethylammonium salt of everninomicin D which is used without further purification in the electrochemical reduction described hereinbelow.

B. In a manner similar to that described in Preparation 1A, treat each of everninomicin C and everninomicin B with tetraethylammonium hydroxide.

Isolate each of the resultant products in a manner similar to that described to obtain everninomicin C tetraethylammonium salt and everninomicin B tetraethylammonium salt, respectively.

C. In the procedures of Preparations 1A and 1B, by substituting for tetraethylammonium hydroxide other tetraalkylammonium hydroxides such as tetrabutylammonium hydroxide and tetramethylammonium hydroxide, there is obtained the corresponding tetraalkylammonium salt of each of the everninomicin antibacterial agents listed therein.

EXAMPLE 1

Determination of Current-Voltage Curves and General Electrolysis Procedure

Current-potential curves of the everninomicins or salts thereof are obtained in 5 ml. portions of approximately millimolar solutions of said everninomicins or derivatives thereof utilizing a Leeds and Northrup recording polarograph (Electrochemograph Type E).

The solutions to be polarographed are prepared by dissolving the everninomicin starting compound in the solvent in which the electrolysis is to be carried out, then adding the electrolyte to be used in the electrolysis. Thus, 3.36 gms. of the tetraethylammonium salt of everninomicin D dissolved in 85 ml. of a 0.01 molar solution of tetraethylammonium fluorborate in anhydrous deoxygenated dimethylformamide under argon yields a polarographic wave having half-wave potential of −1.72 volts vs. the saturated calomel electrode (SCE). The dimethylformamide must be deoxygenated prior to carrying out the polarogram.

The electrolysis cell is a three-electrode system cell consisting of a cylindrical glass cathode compartment with a 1 cm. deep pool of mercury acting as cathode. Contact with the mercury is made through a side arm attached to the cell at a point below the mercury level. The anode compartment is an Alundum cup suspended in the cathode compartment with a graphite anode. The third electrode is a saturated calomel electrode, which is inserted in the cathode compartment with the tip just touching the mercury surface. The electrolysis is carried out, preferentially, using an automatic potentiostat such as the Lingane Jones type (J. J. Lingane et al., Anal. Chem., 22, (1169–1950)), although manual potentiostats may also be used, the electrolytic reduction being carried out until the current measurement decreases to a constant value.

The anolyte and catholyte solutions may be the same or different. Part of the solution to be used in the electrolysis is added to a porous Alundum cup and allow to stand in air or under an inert atmosphere until the cup becomes damp on the outside. The remaining solution is added to the electrolysis cell containing mercury, which is cooled with an ice bath. The gas to be used in the electrolysis (e.g. nitrogen, argon, air or oxygen) is bubbled through both the catholyte and anolyte solutions for about 30–60 minutes, after which the Alundum cup with its graphite anode and containing the anolyte is suspended in the cathode compartment so that the bottom of the cup is near, but not touching, the mercury. A saturted calomel electrode is inserted in the cathode compartment so that the tip just touches the mercury surface. The catholyte solution is stirred and the control potential of the mercury vs. the saturated calomel electrode is set at −1.8 volts until the current approaches a constant value as determined polarographically on deoxygenated aliquots of the electrolyte.

To carry out the electrochemical reduction process of this invention, the everninomicin starting compound to be reduced (e.g. everninomicin D) is added to the catholyte solution and the electrolysis is continued until the current returns to the constant value possessed by the catholyte prior to the addition of the everninomicin as determined polarographically on deoxygenated aliquots of the reduction solutions.

To isolate the mixture of everninomicin derivatives thereby produced, the catholyte solution is evaporated in vacuo and the resultant residue dissolved in an organic solvent and the product mixture separated into its components utilizing chromatographic techniques as described in detail hereinbelow.

EXAMPLE 2

Reduction of Everninomicin D in Anhydrous Dimethylformamide Under an Atmosphere of Argon A. The Electrolysis Dissolve 3.36 gm. of tetraethylammonium salt of everninomicin D in 85 ml. of a 0.01 molar solution of tetraethylammonium fluorobrate in anhydrous dimethylformamide and place the solution in the cathode compartment of the three-electrode cell. In the anode compartment of the cell place a solution of 0.01 molar tetraethylammonium iodide in anhydrous dimethylformamide until the level of the anolyte is at least equal to the level of the catholyte solution. Bubble argon throughout both the catholyte and anolyte at room temperature for about 30 minutes, then electrolyze the solution at room temperature at a cathode potential of about −1.8 volts (vs. SCE) until the current drops to a constant small value.

Evaporate the catholyte in vacuo and dissolve the resultant residue in 120 ml. of methylene chloride. Extract the methylene chloride solution with 120 ml. of phosphate buffer of pH 6.0. Dry the methylene chloride solution over anhydrous sodium sulfate.

B. Densitometric Determination of Product Yields

Dilute a portion of the methylene chloride solution obtained in Example 2A with additional methylene chloride to obtain a solution containing 3.5 mg./ml. of the product mixture. On a 20 × 20 cm. thin layer chromatographic plate pre-coated with silica gel of a 0.25 mm. layer thickness, make spots with identical 10 μl aliquots of the foregoing solution of the reduction products with five alternate spots of 10 μl aliquots of a standard solution containing a mixture of identical amounts of authentic samples of each of everninomicin D, everninomicin D-3, everninomicin D-7 and desevernitrose everninomicin D. Place the spots 2 cm. apart and 2 cm. from the plate edge.

Develop the plate in the lower phase of a chloroform:methanol:water (2:1:1) system for 15 cm. in a pre-equilibrated chromatographic chamber. Apply densitometric analysis to determine the respective yield of each compound in the product mixture which, in this example, is as follows:

Everninomicin D-3 — 59%,
Everninomicin D-7 — 14%,
Desevernitrose everninomicin — 14%.

C. Separation of the Components in the Product Mixture

Evaporate the methylene chloride solution obtained in Example 2A and dissolve the resultant residue in a minimum amount of 30% acetone in benzene. Place the solution in the top of a 2 cm. diameter column containing 134 gm. of silica gel which has been washed with 30% acetone in benzene. Elute the column with 30% acetone in benzene. Combine the like fractions as determined by thin layer chromatography and evaporate each of the like combined fractions in vacuo to obtain each of everninomicin D-3, everninomicin D-7 and desevernitrose everninomicin D having the following physical constants;

Everninomicin D-3:

$[\alpha]_D^{26}$ −29.6° (c=1% chloroform); m.p. 158°–162° C; $\lambda_{max}$ methanol 2294 nm, ($\epsilon$= 5,800); $\lambda_{max}$ methanol-NaOH 295 nm, $\epsilon$ 11,500; Infrated Absorption Spectrum when dissolved in chloroform having peaks at about 2.9. 3.4, 5.75, 6.33, 6.48, 6.87, 7.1, 7.4, 7.7, 8.0, 8.4, 8.5, 9.1, 9.6, 10.3, 10.6 and 11.0 μ;

Nuclear Magnetic Resonance (60 MHz) in deuterochloroform with trimethylsilane (TMS) as internal reference; See FIG. 1;

$R_f$ = 0.45 via thin layer chromatography in chloroform-methanol:water (2:1:1);

Combustion Analysis as follows:

|  | Found (%) | Theory (%) |
| --- | --- | --- |
| Carbon | 52.72 | 53.18 |
| Hydrogen | 6.70 | 6.63 |
| Nitrogen | 0 | 0 |
| Chlorine | 4.65 | 4.76 |

Everninomicin D-7:

$[\alpha]_D^{26}$ −35.6° (chloroform, 2 mg/2ml); m.p. 173°–175° C; $\lambda_{max}$ trifluoroethanol, 213 nm, $\epsilon$ 24,300; 287 nm, $\epsilon$ 5,620;

Infrared Absorption Spectrum in Nujol having peaks at about 5.77, 6.13, 6.37, 6.85, 7.27, 8.0, 8.35; 9.1 (broad), 9.6 (broad), 10.27, 10.53, 11.0, 11.45, 11.95, 13.0, 13.55, and 13.85 μ;

$R_f$ = 0.2 via thin layer chromatography in a chloroform-methanol:water (2:1:1) system; Nuclear Magnetic Resonance (60 MHz) in deuterochloroform with TMS as internal reference; see FIG. 2; Combustion Analysis as follows:

|  | Found (%) | Theory (%) |
| --- | --- | --- |
| Carbon | 52.06 | 52.55 |
| Hydrogen | 6.90 | 6.68 |
| Nitrogen | 0 | 0 |
| Chlorine | 4.41 | 4.70 |

Desevernitrose Everninomicin D:

$[\alpha]_D^{26}$ −0.5° (Chloroform); m.p. 179°–181° C; Neutralization Equivalent = 1410; pKa = 7.5; $\lambda_{max}$ trifluoroethanol 205 nm; ($\epsilon$=32,783).

Infrared Spectrum (Nujol) = 2.9, 3.4, 5.7, 6.1, 6.3, 7.9, 8.3, 9.0, 9.6, 10.2, 10.5, 11.0. 13.5; (chloroform) 2.9, 3.3, 3.4, 5.7, 6.2, 6.3, 6.4, 7.1, 7.2, 7.7, 8.0, 9.0, 9.6, 10.3, 10.6, 11.0 μ.

$R_f$ = 0.3 via thin layer chromatography in a chloroform:methanol:water (2:1:1) system:

Combustion Analysis as follows:

|  | Found (%) | Theory (%) |
| --- | --- | --- |
| Carbon | 51.76 | 51.60 |
| Hydrogen | 6.48 | 6.42 |
| Nitrogen | 0 | 0 |
| Chlorine | 5.45 | 5.25 |

D. In the procedures of Examples 2A, 2B and 2C, by substituting for everninomicin D other starting compounds such as a salt of everninomicin D, e.g. the tetraethylammonium salt, there is obtained a product mixture comprising everninomicin D-3, everninomicin D-7 and desevernitrose everninomicin D. E. In the procedures of Examples 2A, 2B and 2C, by utilizing as starting compounds the corresponding derivatives of everninomicin B and everninomicin C, there is obtained the corresponding product mixtures comprising everninomicin B-3, everninomicin B-7, and deservernitrose everninomicin B or the corresponding product mixture comprising everninomicin C-3, everninomicin C-7 and desevernitrose everninomicin C, each of which may be isolated and purified in the manner described in Examples 2A, 2B and 2C to obtain each of the everninomicin B or C derivatives present in the product mixture.

EXAMPLE 3

Reduction of the Tetraethylammonium Salt of Everninomicin D in Anhydrous Dimethylformamide in the Presence of Oxygen In a manner similar to that described in Example 2A, prepare a solution of 1 mg. of the tetraethylammonium salt of everninomicin D in 100 ml. of a 0.01 molar solution of tetraethylammonium fluoborate in anhydrous dimethylformamide and place the solution in the cathode compartment of the three-electrode cell. Add a 0.01 molar solution of tetraethylammonium fluoborate in anhydrous dimethylformamide to the anode compartment until the level of the anode is at least equal to the level of the cathode solution. Bubble air through both the anolyte and catholyte for about an hour, then electrolyze the solution at a cathode potential of about −1.8 volts (vs. SCE). Isolate the resultant product mixture in a manner similar to that described in Example 2B and 2C to obtain everninomicin D-3 (13% theory), everninomicin D-7 (13% theory), and desevernitrose everninomicin D (4% theory).

EXAMPLE 4

Electrochemical Reduction of the Tetraethylammonium Salt of Everninomicin D in Anhydrous dimethylformamide in the Presence of Oxygen In a manner similar to that described in Example 2A, dissolve 101 mg. of tetraethylammonium salt if everninomicin D in 100 ml. of a 0.01 molar solution of sodium fluoborate in anhydrous dimethylformamide and place the solution in the cathode compartment of the three-electrode cell. Add a 0.01 molar solution of sodium fluoborate in anhydrous dimethylformamide to the anode compartment until the level of the anolyte is at least equal to the level of the catholyte solution. Bubble air through both the catholyte and anolyte for about an hour, then electrolyze the solution at a cathode potential of about −1.8 volts (vs. SCE) while continuing to bubble air through the anolyte and catholyte solutions. Isolate the resultant product mixture in a manner similar to that described in Examples 2B and 2C to obtain, respectively, everninomicin D-3 (32% theory) and everninomicin D-7 (12% theory).

EXAMPLE 5

Electrochemical Reduction of the Tetraethylammonium Salt of Everninomicin D in Anhydrous Acetonitrile in the Presence of Oxygen Prepare a solution of 75 mg. of tetraethylammonium salt of everninomicin D in 100 ml. of a 0.01 molar solution of tetraethylammonium fluoborate in acetonitrile. Place the solution in the cathode compartment, then add a 0.01 molar solution of tetraethylammonium fluoborate in acetonitrile to the anode compartment until the level of the anode is at least equal to the level of the cathode solution. Bubble air through both the catholyte and anolyte solution for about an hour, then electrolyze the solution at a cathode potential of about −1.8 volts (vs. SCE). In similar manner to that described in Examples 2B and 2C, isolate and purify each of the products in the resultant product mixture to obtain, respectively, everninomicin D-3 (18% theory), and everninomicin D-7 (18% theory).

EXAMPLE 6

N-Methylglucamine Salt of Everninomicins B-3, B-7, C-3, C-7, D-3 and D-7

A. To 300 mg. of everninomicin D-7 dissolved in 1.5 ml. of methanol, add 40 mg. of N-methylglucamine and stir the reaction mixture at room temperature for 1½ hours. Slowly add ether (40 ml.) with good agitation. Separate the resultant precipitate by filtration and air dry to give 175 mg. of everninomicin D-7 N-methylglucamine. B. Similarly, treat each of everninomicin D-3, everninomicin B-3 and everninomicin B-7, everninomicin C-3 and everninomicin C-7 with N-methylglucamine in methanol. Isolate each of the resultant products in a manner similar to that described in Example 6A to obtain everninomicin D-3 N-methylglucamine, everninomicin B-3 N-methylglucamine, everninomicin B-7 N-methylglucamine, everninomicin C-3 N-methylglucamine and everninomicin C-7 N-methylglucamine, respectively.

EXAMPLE 7

Alkali Metal Salts of Everninomicins D-3, D-7, C-3, C-7, B-3 and B-7

A. Sodium Salt of Everninomicin D-7

To a vigorously stirred suspension of 1 g. of everninomicin D-7 in 25 ml. of water under a nitrogen atmosphere, slowly add 0.1 N sodium hydroxide (about 6.8 ml.) until the pH of the reaction mixture is 9.5 and the solid is in solution. Stir at room temperature for an additional hour (final pH about 8.5). Lyophilize the clear solution to obtain everninomicin D-7 sodium salt as a white solid.

B. In a manner similar to that described in Example 7A, treat each of the following with 0.1 N sodium hydroxide.
everninomicin D-3,
everninomicin C-3,
everninomicin C-7,
everninomicin B-3, and
everninomicin B-7.

Isolate and purify the resultant products in a manner similar to that described in Example 7A to obtain, respectively,
everninomicin D-3 sodium salt,
everninomicin C-3 sodium salt,
everninomicin C-7 sodium salt,
everninomicin B-3 sodium salt, and
everninomicin B-7 sodium salt.

C. In the above procedures, substitute for the sodium hydroxide, equimolar quantities of other alkali metal hydroxides, (e.g. potassium hydroxide and lithium hydroxide) to obtain the corresponding potassium and lithium salts.

The present invention includes within its scope pharmaceutical compositions comprising one or a mixture of everninomicins B-3, B-7, C-3, C-7, D-3 and D-7 or of a pharmaceutically acceptable mono-cationic or N-methylglucamine salt thereof in association with a compatible, pharmaceutically acceptable carrier or coating. Also included within our invention is the method of eliciting an antibacterial response in a warm-blooded animal having a susceptible bacterial infection which comprises administering to said animal a non-toxic antibacterially effective amount of a member selected from the group consisting of everninomicin B-3, everninomicin B-7, everninomicin C-3, everninomicin C-7, everninomicin D-3, and everninomicin D-7 and pharmaceutically acceptable mono-cationic and N-methylglucamine salts of the foregoing.

The compositions may be administered parenterally, orally or topically, parenteral administration being preferred. In carrying out the methods of this invention, the active ingredient is normally combined with conventional pharmaceutical diluents and carriers which are based upon the desired route of administration. The parenteral route is preferred, particularly with salts of everninomicin D-3 and D-7, due to the increased absorption thereof when administered parenterally. In carrying out the method, the active everninomicin derivative can, if desired, be combined with other therapeutically active compositions customarily included in antibacterial formulations.

The individual unit dosage and frequency of administration is determined not only by the nature and severity of the bacterial infection for which relief is sought, but also upon age, weight, species, underlying physical condition and route of administration. The exact amount to be administered should be non-toxic, yet pharmaceutically effective in alleviating the symptoms of bacterial infections. Generally, for the treatment of bacterial infections, the compositions are administered parenterally so as to give a daily dose of from 1 to about 15 mg/kg of an everninomicin 3 or 7 compound of this invention.

The following examples illustrate pharmaceutical compositions according to the invention.

EXAMPLE 9

| Parenteral Solution of Everninomicin D-3 | |
|---|---|
| | mg/ml |
| Everninomicin D-3 sodium salt | 58.00 |
| Sodium chloride | 5.00 |
| Sodium bisulfite | 1.625 |
| Sodium hydroxide | 0.56 |
| Purified water, q.s. | 1.0 ml |

Procedure

Sparge with nitrogen about 90% of the required amount of water. With stirring, add the sodium chloride and sodium bisulfite and stir under dissolved. Add the everninomicin D-7 sodium salt and with stirring add 1 N sodium hydroxide until the solution reaches a pH of 8.7. Adjust volume with purified water. Filter through a sterilizing membrane. With this solution, fill multiple dose vials. Lyophilize.

EXAMPLE 10

| Parenteral Solution of N-Methylglucamine Salt of Everninomicin D-7 | |
|---|---|
| | mg/ml |
| Everninomicin D-7 N-methylglucamine salt | 58.00 |
| Sodium Chloride | 5.0 |
| Sodium Bisulfite | 1.625 |
| Sodium Hydroxide | 0.56 |
| Methylparaben | 1.8 |
| Propylparaben | 0.2 |

| -continued | |
|---|---|
| Parenteral Solution of N-Methylglucamine Salt of Everninomicin D-7 | |
| | mg/ml |
| Purified water, q.s. | 1.0 ml. |

Procedure

Sparge with nitrogen about 90% of the required amount of water and heat the water to a temperature of about 60°–70° C. Add the methylparaben and propylparaben, stir until dissolved, then cool the solution to 25°–30° C. Then follow the procedure described in Example 9.

EXAMPLE 11

| Parenteral Suspension of Everninomicin D-7 | |
|---|---|
| Parenteral Suspension: | mg/ml |
| Everninomicin D-7 | 50. |
| Sodium carboxymethylcellulose | 1.5 |
| Polysorbate 80 U.S.P. | 0.5 |
| Methylparaben | 1.8 |
| Propylparaben | 0.2 |
| Water, q.s. | 1.0 ml. |

Procedure

1. Prepare a solution of sodium carboxymethylcellulose, Polysorbate 80, U. S. P., methylparaben, and propylparaben.

2. Aseptically, slurry everninomicin D-7 with a portion of the above vehicle and pass through a colloid mill.

3. Mix the milled slurry with the remainder of the vehicle.

4. Fill into sterile vials.

We claim:

1. A compound selected from the group consisting of an everninomicin derivative devoid of nitrogen represented by the following formula, and the pharmaceutically acceptable phenolic mono-cationic salts and N-methylglucamine acid addition salts thereof:

-continued (I)

wherein
X is a member selected from the group consisting of

Y is a member selected from the group consisting of hydrogen and hydroxyl;
Z is a member selected from the group consisting of and hydrogen provided Y is hydrogen; and said pharmaceutically acceptable salts are salts of the phenol substituent in said everninomicin derivative.

2. A compound of claim 1 which is the sodium salt of an everninomicin derivative represented by the formula therein.

3. A compound of claim 1 which is the N-methyl-glucamine acid addition salt of an everninomicin derivative represented by the formula therein.

4. A compound of claim 1 wherein X is

Figure 1:
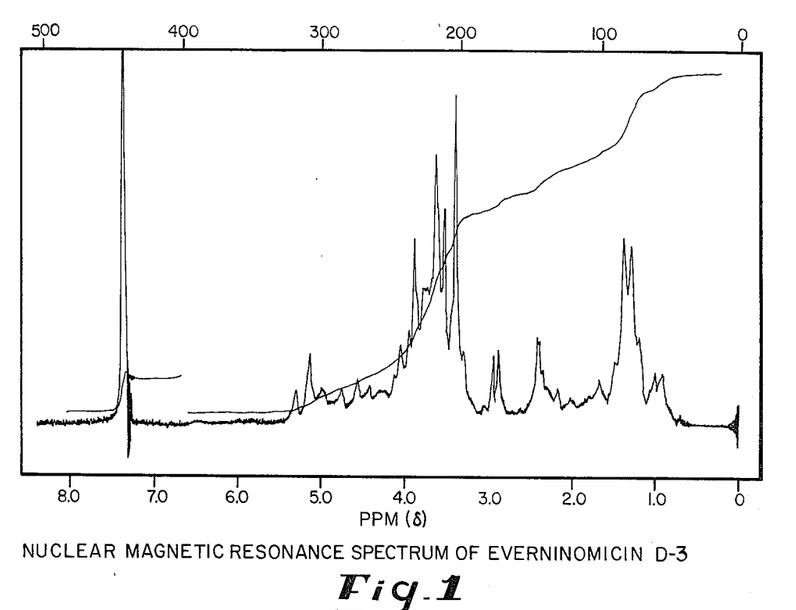

Y is hydrogen and Z is said compound being everninomicin D-3, effective in inhibiting the growth of gram-positive bacteria and having the following physical characteristics: an $R_f =$ 0.45 via thin layer chromatography in chloroform:methanol:water (2:1:1) system; the following elemental analysis: C=52.72%; H=6.70%; N=0.0%; Cl=4.65%; a specific rotation of about −29.6° as measured in chloroform at 1% concentration by the D-line of sodium at 26° C; a melting point of about 158°–162° C when measured on a Fisher-John block; an ultraviolet absorption maxima at 294 nm with ε in methanol equal to about 5,800 and at 295 nm with ε in methanol:sodium hydroxide equal to about 11,500; an infrared absorption spectrum when dissolved in chloroform having peaks at about 2.9, 3.4, 5.75, 6.33, 6.48, 6.87, 7.1, 7.2, 7.4, 7.7, 8.0, 8.4, 8.5, 9.1, 9.6, 10.3, 10.6 and 11.0 μ; a nuclear magnetic resonance (60 MHz) spectrum in deuterochloroform with trimethylsilane as internal reference substantially as shown in FIG. 1; and an antibacterial spectrum including the bacteria enumerated in Table I.

5. A compound of claim 1 which is the sodium salt of everninomicin D-3.

6. A compound of claim 1 which is the N-methyl-glucamine acid addition salt of everninomicin D-3.

7. A compound of claim 1 wherein X is

Figure 2:
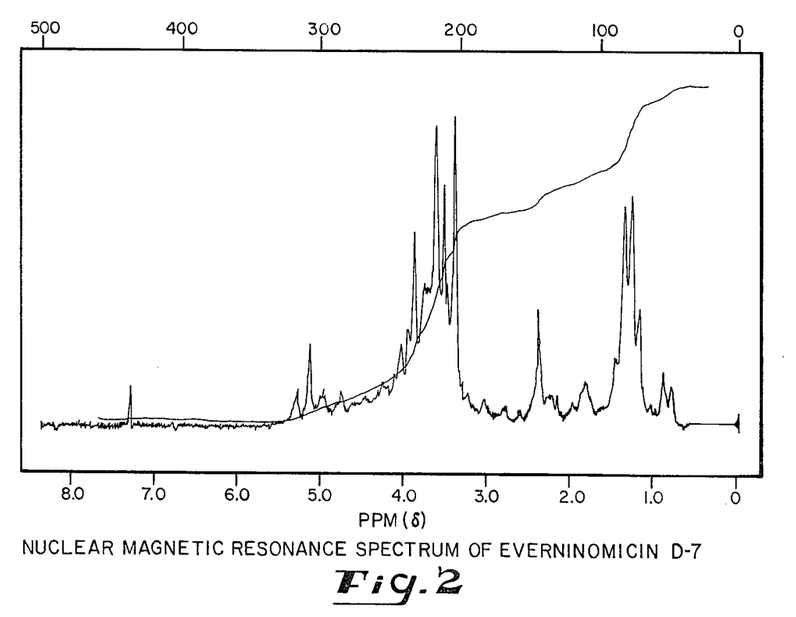

Y is hydrogen, and Z is said compound being everninomicin D-7, effective in inhibiting the growth of gram-positive bacteria and having the following physical characteristics: an $R_f =$ 0.2 via thin layer chromatography in a chloroform:methanol:water (2:1:1) system; the following elemental analysis: C=52.06%: H=6.90%; N=0.0%; Cl=4.41%; a specific rotation of about −35.6° as measured in chloroform at 2 mg/2 ml concentration; a melting point of about 173°–175° C when measured on a Fisher-John block; an ultraviolet absorption maximum at 213 nm with ε in trifluoroethanol equal to about 24,300; an infrared absorption spectrum when suspended in Nujol having peaks at about 5.77, 6.13, 6.37, 6.85, 7.27, 8.0, 8.35, 9.1 (broad), 9.6 (broad), 10.27, 10.53, 11.0, 11.45, 11.95, 13.0, 13.55, and 13.85 μ; a nuclear magnetic resonance spectrum (60 MHz) in deuterochloroform with trimethylsilane as internal reference substantially as shown in FIG. 2; and an antibacterial spectrum including the bacteria enumerated in Table I.

8. A compound of claim 1 which is the sodium salt of everninomicin D-7.

9. A compound of claim 1 which is the N-methyl-glucamine acid addition salt of everninomicin D-7.

10. The method of eliciting an antibacterial response in a warm-blooded animal having a susceptible bacterial infection, which comprises administering to said animal a non-toxic, antibacterially effective amount of a member selected from the group consisting of an everninomicin derivative devoid of nitrogen represented by the following formula, and the pharmaceutically acceptable phenolic mono-cationic salts and N-methylglucamine acid addition salts thereof:

wherein X is a member selected from the group consisting of

Y is a member selected from the group consisting of hydrogen and hydroxyl;

Z is a member selected from the group consisting of and hydrogen provided Y is hydrogen; and said pharmaceutically acceptable salts are salts of the phenol substituent in said everninomicin derivative.

11. A pharmaceutical composition comprising an antibacterially effective amount of a member selected from the group consisting of an everninomicin derivative devoid of nitrogen represented by the following formula, and the pharmaceutically acceptable phenolic mono-cationic salts and N-methylglucamine acid addition salts thereof:

and hydrogen provided Y is hydrogen; and said pharmaceutically acceptable salts are salts of the phenol substituent in said everninomicin derivative; together with a non-toxic pharmaceutically acceptable carrier.

* * * * *

UNITED STATES PATENT OFFICE
CERTIFICATE OF CORRECTION

Patent No. 4,027,016                  Dated May 31, 1977

Inventor(s) Peter Kabasakalian, et al

It is certified that error appears in the above-identified patent and that said Letters Patent are hereby corrected as shown below:

Column 6, line 60, "the everninomicin B," should read ---in everninomicin B,---. Column 10, line 37, "amount 0.3 to" should read ---about 0.3 to---. Column 12, line 17, "fluorborate" should read ---fluoborate---. Column 13, line 13, "fluoroborate" should read ---fluoborate---. Column 15, line 16, "1 mg." should read ---1 gm.---; line 39, "salt if" should read ---salt of---.

Signed and Sealed this

Twentieth Day of September 1977

[SEAL]

Attest:

RUTH C. MASON            LUTRELLE F. PARKER
*Attesting Officer*      *Acting Commissioner of Patents and Trademarks*